(12) United States Patent
Maschke (10) Patent No.: US 8,208,990 B2
(45) Date of Patent: Jun. 26, 2012

(54) CATHETER DEVICE

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1239 days.

(21) Appl. No.: 11/636,952

(22) Filed: Dec. 11, 2006

(65) Prior Publication Data

US 2007/0135712 A1 Jun. 14, 2007

(30) Foreign Application Priority Data

Dec. 12, 2005 (DE) .................. 10 2005 059 262

(51) Int. Cl.
*A61B 5/05* (2006.01)

(52) U.S. Cl. ........ 600/424; 600/407; 600/433; 600/462; 600/466

(58) Field of Classification Search .................. 600/411, 600/407, 410, 422, 423, 433, 462, 466, 467, 600/420, 424, 427; 606/159
See application file for complete search history.

(56) References Cited

U.S. PATENT DOCUMENTS

| | | | |
|---|---|---|---|
| 5,540,959 A | 7/1996 | Wang | |
| 5,752,513 A | 5/1998 | Acker et al. | |
| 5,827,997 A | 10/1998 | Chung et al. | |
| 5,865,748 A | 2/1999 | Co et al. | |
| 5,895,402 A | 4/1999 | Hundertmark et al. | |
| 6,233,476 B1 | 5/2001 | Strommer et al. | |
| 6,298,261 B1 | 10/2001 | Rex | |
| 6,377,048 B1 | 4/2002 | Golan et al. | |
| 6,546,271 B1 | 4/2003 | Reisfeld | |
| 6,600,319 B2 | 7/2003 | Golan | |
| 6,673,999 B1 | 1/2004 | Wang et al. | |
| 6,704,594 B1 | 3/2004 | Blank et al. | |
| 6,813,512 B2 | 11/2004 | Aldefeld et al. | |
| 7,734,009 B2 | 6/2010 | Brunner | |
| 2002/0007215 A1 | 1/2002 | Falotico et al. | |
| 2002/0019644 A1* | 2/2002 | Hastings et al. | 606/159 |
| 2005/0004663 A1* | 1/2005 | Llanos et al. | 623/1.46 |
| 2005/0113686 A1 | 5/2005 | Peckham | |
| 2005/0124898 A1* | 6/2005 | Borovsky et al. | 600/467 |
| 2005/0182295 A1* | 8/2005 | Soper et al. | 600/117 |
| 2005/0187571 A1 | 8/2005 | Maschke | |
| 2005/0203553 A1 | 9/2005 | Maschke | |
| 2005/0203558 A1 | 9/2005 | Maschke | |
| 2006/0241484 A1* | 10/2006 | Horiike et al. | 600/467 |
| 2006/0246107 A1 | 11/2006 | Harder et al. | |
| 2007/0038075 A1 | 2/2007 | Maschke | |
| 2007/0066890 A1 | 3/2007 | Maschke | |

(Continued)

FOREIGN PATENT DOCUMENTS

DE 40 37 586 A1 5/1992

(Continued)

OTHER PUBLICATIONS

R.J. Dickinson and R.I. Kitney, "Miniature ultrasonic probe construction for minimal access surgery", Physics in Medicine and Biology, vol. 49, 2004, pp. 3527-3538.

(Continued)

*Primary Examiner* — Brian Casler
*Assistant Examiner* — Daniel Huntley (57) ABSTRACT

The invention relates to a catheter device for performing atherectomy, comprising an atherectomy catheter, an IVMRI sensor, position sensors and an image-processing unit which is fashioned for generating combined 2D and/or 3D image recordings based on the data from the sensors.

18 Claims, 4 Drawing Sheets

U.S. PATENT DOCUMENTS

| | | | |
|---|---|---|---|
| 2007/0106146 A1* | 5/2007 | Altmann et al. | 600/407 |
| 2007/0123771 A1* | 5/2007 | Redel et al. | 600/407 |

FOREIGN PATENT DOCUMENTS

| | | |
|---|---|---|
| DE | 198 52 467 A1 | 7/1999 |
| DE | 100 51 244 A1 | 5/2002 |
| DE | 102 53 634 A1 | 5/2004 |
| DE | 10 2004 008 368 B4 | 5/2006 |
| DE | 10 2004 008 371 B4 | 5/2006 |
| EP | 0 993 804 A1 | 4/2000 |
| EP | 1 088 515 A1 | 4/2001 |
| WO | WO 00/13586 A1 | 3/2000 |
| WO | WO 2005/067392 A2 | 7/2005 |

OTHER PUBLICATIONS

Biophan Technologies, Inc., "Biophan Technologies Announces Nanview™ Technology", Dec. 17, 2003, pp. 1-2.

Invention Disclosure citing listed references, Aug. 26, 2005, pp. 1-3.

* cited by examiner

FIG 5

CATHETER DEVICE

CROSS REFERENCE TO RELATED APPLICATIONS

This application claims priority of German application No. 10 2005 059 262.7 filed Dec. 12, 2005, which is incorporated by reference herein in its entirety.

FIELD OF THE INVENTION

The invention relates to a catheter device for performing atherectomy.

BACKGROUND OF THE INVENTION

Vascular diseases are among the most common fatal diseases. They include, above all, myocardial infarction, which is caused by diseases of the coronary arteries. Where a blockage of coronary arteries occurs as a result of arteriosclerotic plaque, this clinical picture is treated mainly by means of percutaneous transluminal coronary angioplasty (PTCA). Here, the constricted points in the coronary arteries are expanded by means of a balloon catheter. However, clinical studies have shown that this leads in very many patients to a restenosis, and in some of the studies such restenosis formed in 50% of patients. High-frequency rotor ablation angioplasty, which can advantageously be used in particular in fibrotic or calcified or elongated stenoses has been known as an alternative method for some years.

In order to reduce the risk of formation of restenosis, coronary atherectomy is used to achieve rechanneling of stenosed coronary arteries through debulking. The device for performing the atherectomy is a catheter system with a metal casing in which the actual cutting apparatus, the cutter, is located. The cutter, which consists of a conically ground blade, is connected via a flexible connection to a motor outside the patient. The cutting blade is driven by this motor at a speed of 1,500-2,000 rpm. A balloon is mounted on one side of the metal housing, and a window on the contralateral side. During the atherectomy, the balloon is inflated, and the openings and the blade are thereby pressed into the plaque. The rotating blade can now be pushed forward from the outside toward the tip of the atherectomy housing. By this means, the plaque is cut out and the plaque material pushed toward the tip of the atherectomy device. The balloon is then deflated, the atherectomy device rotated a little so that the window points toward another area of the plaque, and the process is repeated. An atherectomy device is known from U.S. Pat. No. 5,895,402.

In U.S. 2005/0203553 A1 a catheter with an integrated OCT sensor for deployment in blood vessels has been proposed, which improves image representation of the stenosis in the near range.

A new imaging method, which is already being trialed in individual clinics, is intravascular magnetic resonance tomography (IVMRI), which is known, for example, from printed publications U.S. Pat. No. 6,377,048, U.S. Pat. No. 6,704,594 and U.S. Pat. No. 6,600,319. The first-mentioned printed publication describes a solution with the aid of an external (i.e. applied outside the body) static magnetic field. In the two last-mentioned printed publications, solutions are described in which the static magnetic field is generated by the catheter and no external magnetic field is required for generating a field. In the case of IVMRI, an MRI catheter, i.e. a catheter for imaging with the aid of magnetic resonance signals, is introduced into vessels under X-ray monitoring and extracted from the vessels manually. Important additional medical information about arteriosclerotic plaque can be obtained through the images of the IVMRI systems. Magnetic resonance imaging is known for its good representation of soft tissue.

In U.S. 2005/018571A1 a device for performing and monitoring artherectomy is described in which an externally rotatingly driven cutting blade, set back so as to protrude into an opening of the catheter tip, can be pressed onto the vessel wall by means of an inflatable balloon arranged on the side opposite the window opening of the catheter sheath, an artherectomy catheter being connected with an OCT catheter to form an integrated assembly.

SUMMARY OF THE INVENTION

Common to all the known solutions is the fact that they each solve only individual problems. It has until now, however, not been possible to integrate conventional catheters in an optimum manner into the medical workflow.

The object of the invention is therefore to indicate a catheter device which is better integrated into the medical workflow and permits optimal diagnostic imaging within the framework of minimally invasive medical treatment.

In order to achieve this object, there is provided according to the invention a catheter device of the type mentioned in the introduction that comprises an atherectomy catheter, an IVMRI sensor, position sensors and an image-processing unit which is fashioned for generating combined 2D and/or 3D image recordings based on the data from the sensors.

The invention is based upon the recognition that until now only separately known catheters can be combined to form an integrated assembly, whereby an IVMRI sensor and position sensors are used and the image information obtained therefrom superimposed in a 2D representation or used to create a 3D image recording. The IVMRI sensor enables image data recording using the technology of intravascular magnetic resonance imaging, which can provide important information about the arteriosclerotic plaque and enables a good representation of soft tissue.

The catheter of the catheter device can according to the invention comprise a lumen for introducing an MRI contrast medium. Through the use of MRI contrast medium, i.e. of contrast medium which is specifically intended for magnetic resonance imaging, the recording of data can be improved. The contrast medium is guided through a lumen or a channel in the catheter directly to the organ or vessel of interest. Possible MRI contrast media are, for example, contrast media based on gadolinium.

More recent developments in nanotechnology can also be used to enhance image quality. In this way, the disadvantage which has existed until now of the long time delay in introducing the contrast medium through a peripheral vein is avoided.

It is preferable if the catheter device according to the invention is integrated in a medical treatment device, in particular an X-ray device. Such an angiographic or cardiological X-ray installation comprising a high-voltage generator, X-ray source, radiation cover, image-detector unit, patient bed, source and detector stands and a digital image system enables the creation of angiographic X-ray images and of image recordings in the manner of computer-tomography recordings and is capable of processing, displaying and superimposing the information supplied by the catheter device according to the invention.

In the catheter device according to the invention, a magnetic control, but alternatively also a mechanical control can be provided, which preferably has pulling wires in order to deflect the catheter tip. In this way, the tip of the catheter can be deflected to one side.

It can also be provided that the catheter can be controlled by means of an external magnetic field, the catheter comprising at least one permanent magnet and/or at least one electromagnet. In a further embodiment of the invention, the receiver coils can have iron cores and optionally be usable as a receiving antenna or as an electromagnet for magnetic navigation.

In order to achieve miniaturization of the catheter, it is not necessary for the coils to be arranged orthogonally to one another, instead said coils can also be arranged at a random angle, in particular approximately 60°.

The catheter device can also comprise an OCT sensor and/or an IVUS sensor. In this case, optical coherence tomography (OCT) and intravascular ultrasound (IVUS) optionally provide one or two further image recording possibilities for achieving a good representation of the vessel constriction. The combination of OCT and IVUS makes good image representation possible in various distance ranges. In this way, a combination of different imaging methods enables good representation of soft tissue as well as optimal representation in the near range and in the far range coupled with good locational or spatial resolution. Combination with at least one other imaging method such as OCT or IVUS makes it possible to identify both the plaque and the vessel wall better during treatment, as a result of which treatment errors can be avoided.

In the catheter device according to the invention, the IVMRI sensor and/or optionally the OCT sensor and/or the IVUS sensor can be oriented laterally, relative to the longitudinal axis of the catheter. Accordingly, the IVMRI sensor and optionally the OCT sensor and the IVUS sensor can be separately or jointly rotatable about the longitudinal axis of the catheter. Alternatively, however, multiple fixed sensors, distributed on the periphery, can also optionally be provided, which sensors are interrogated consecutively. It is also possible for the catheter to be capable of being advanced or retracted at a specifiable speed by means of a drive unit. In this way, three-dimensional image recordings can be produced.

Within the context of image processing, the image-processing unit of the catheter device according to the invention can be fashioned for approximating the center line and/or the envelope curve of a body part under examination, in particular of a vessel. The vascular envelope curve can be used in further image post-processing steps. For example, with the aid of the envelope curve, the three-dimensional IVMRI or IVMRI-OCT-IVUS image recordings or image recordings from a different combination of image-recording methods, comprising IVMRI, with other anatomical image data, originating, say, from a 3D-angiographic system, can be registered and then displayed in a fused manner. To do this, the 3D image recordings of the catheter and the anatomical image data are advantageously translated to a common system of coordinates.

In order in the catheter device according to the invention to prevent motion artefacts, which occur, for example, as a result of respiration and the movement of the heart or of other organs, the frequency and/or the amplitude of the movement can be recorded and corrected computationally.

In order to avoid interference in the recording of signals from the sensors, it can be provided that it be possible for the sensors to be read out in temporally offset cycles. For example, X-ray detectors and an optionally present electrocardiogram cannot be read out when the transmitters of the electromagnetic position system are active. The IVMRI or optionally present OCT sensors and the position sensors are not read out when the X-radiation is active. Thus, in each case, only those signals are recorded which are not affected by interference.

Particularly good results can be achieved if the catheter device according to the invention has a coating for shielding against electromagnetic fields. Such a coating can comprise a thin-film layer composed of conductive nanoparticles.

In order to avoid any risk to the patient from the mains voltage, the catheter and its sensors can be galvanically isolated from the mains voltage.

In order to facilitate localization of the catheter by means of radiographs, the catheter can have X-ray markers.

In order to reduce the frictional resistance of the catheter during movement inside a vessel, it can be furnished with a coating, which preferably consists of a silicon material and/or nanomaterials. To aid positioning, the catheter can have, particularly at its tip, an inflatable balloon.

In order optionally to emit a warning at raised temperatures, the catheter can have a temperature sensor, arranged preferably at the tip, and optionally also a pressure sensor.

In addition, the catheter device has a premounted stent, which serves in supporting the vessel. By virtue of the fact that such a stent, by which of course is also meant multiple separate devices or stents serving to support a vessel, is also arranged on the one integrated catheter, there is no longer a need for a catheter, which was used, for example, for eliminating plaque as part of atherectomy, to be removed again. The stent can be introduced by means of the catheter device simultaneously with the treatment tools for the atherectomy. There follows from this a significantly reduced risk of restenosis.

Overall, treatment is in this way possible using a single catheter, with which it is possible both to remove the vascular occlusion under appropriate image monitoring by means of IVMRI and optionally other methods and to insert into the vessel a stent which maintains the opening. The treatment consequently necessitates fewer treatment steps while the facility also exists for monitoring the process with three-dimensional recordings. A good representation of soft tissue is ensured while at the same time adequately good images of deeper-lying tissue layers are obtained e.g. through IVUS. By utilizing the signals of the position-sensor system, the arrangement and movement of the integrated treatment catheter can be mapped with the aid of the IVMRI and the said, for example electromagnetic, signals of the position-sensor system, so that the X-radiation to which the patient is exposed can be reduced. In addition, OCT and IVUS signals can be recorded.

The stent can be premounted in the region of the tip of the catheter. Consequently, the device for supporting the vessel is from the outset located in the treatment area so that the stent can then be placed at the correct point at which the treatment has taken place without any major catheter movement.

An expandable balloon can also be provided in the region of the tip of the catheter, it being possible for the premounted stent to be positioned and/or fixed depending on the expansion of the balloon. When the balloon is inflated, the stent is in this way, for example, pressed into the vascular wall and thereby fixed. The stent can be arranged on the balloon when in the non-deployed state, or it is located in the region of the balloon so that when the balloon is expanded by being fed with compressed air, the arrangement of the stent in relation to the vessel is affected. For example, the stent can, when the balloon is deployed, be deformed beyond its elastic limits or overexpanded such that the shape which has been produced as a result of inflation of the balloon remains afterwards. By this means, the stent is selectively shaped and arranged with the aid of the balloon and fixed or anchored in the vascular area.

The stent can also be fashioned so as to be at least partially self-deploying. In this case, for example, an envelope made from a synthetic material and surrounding the stent at least partially is removed, whereupon the corresponding area of the stent deploys. As a rule, either a stent which deploys with the aid of a balloon is used or a self-deploying stent. It is, however, also conceivable to combine these two options for introducing and fixing the stent in the vascular region.

In addition, the stent can be fashioned at least in part from metal, in particular from fine steel or nitinol. As a rule, grid-like or net-like arrangements are used for stents, said arrangements being composed, for example, of steel or a certain metal or other metal alloys, for example the nickel-titanium alloy nitinol.

Furthermore, the stent can be fashioned at least in part from bioresorbable material, in particular from biological material and/or magnesium and/or bio-engineering material and/or plastic. For example, polymers can be used. In the case of bioresorbable materials, there is the advantage that these dissolve after a certain, possibly predefined, time so that the stent, if it is no longer required for vascular support after a certain period, can be automatically disintegrated and thereby removed without any further intervention and without presenting a risk to the patient. Of course, further advantageous materials and combinations of materials can be used for the stent, which can have positive effects on the inside surface of the vessel or can support the vessel and can maintain its opening. In addition, requirements with regard to the options for introducing it and for rendering it visible, for example for control examinations must be complied with. Also, the properties of the stent materials must be noted with regard to their effect on the flow of blood and the development of blood clots.

The stent is advantageously fashioned with a coating, in particular with a nano-coating and/or an active-agent coating. With such coatings, for example, the guidance of the catheter device, on which the stent or the stents are premounted, can be improved. A coating with active agents or drugs which are released over a defined period or at a defined point in time, is used, for example, in order to monitor the cell division of cells in the vascular wall. Corresponding active agents or drugs which are emitted as soon as the stent is placed in the vascular region can also further reduce the risk of restenosis.

The active-agent coating can contain sirolimus and/or paclitaxel and/or everolimus and/or rapamycin and/or FK 506 and/or another growth inhibitor. If required, combinations of active agents can be used.

Furthermore, the catheter can be fashioned with an automatic advancing and/or retracting device. With this, it is possible to insert the integrated catheter into the vessels at a defined speed or to guide it out again from said vessels, as a result of which, for example, complications through too hasty or inaccurate manual guidance can be avoided.

In addition, the invention relates to a medical treatment device, in particular an X-ray device. The inventive treatment device comprises a catheter device of the type described.

In addition, the invention relates to a method for generating examination images in the performance of atherectomy. The method according to the invention is characterized in that an atherectomy catheter is used which has an IVMRI sensor and position sensors, combined 2D and/or 3D image recordings, based on the data from the sensors, being generated by an image-processing unit. Furthermore, the atherectomy catheter optionally has an OCT sensor and/or an IVUS sensor.

BRIEF DESCRIPTION OF THE DRAWINGS

Further advantages and details of the invention will be explained with the aid of exemplary embodiments with reference to the Figures. The Figures are schematic diagrams, in which.

DETAILED DESCRIPTION OF THE INVENTION

Figure 1:
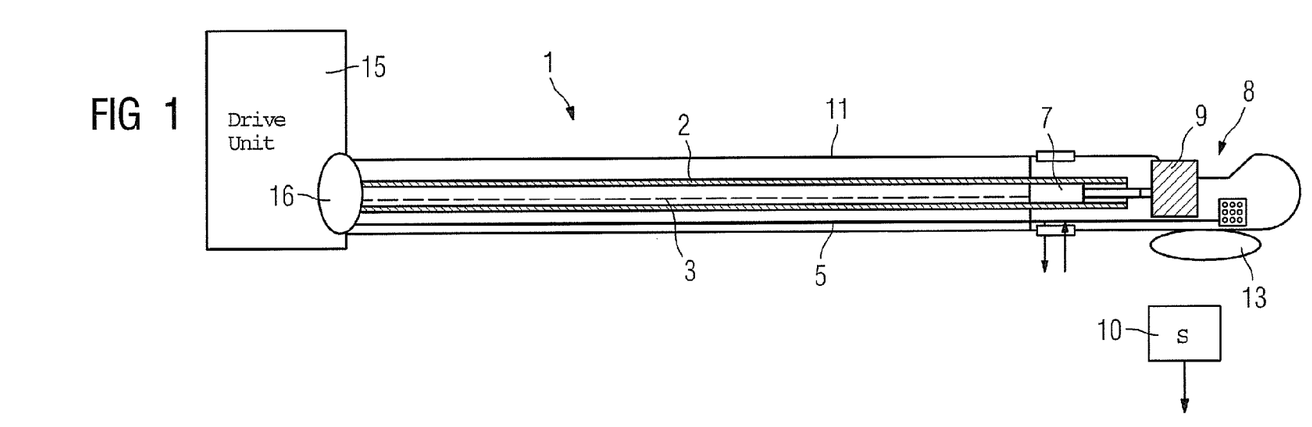
FIGS. 1 and 2 show catheter devices according to the invention for performing atherectomy.

FIG. 1 shows a catheter device 1 according to the invention, said catheter device being fashioned as an atherectomy catheter. The catheter device according to the invention 1 has a hollow flexible drive shaft 2, in which an IVMRI signal line 3 is integrated. Also arranged in the flexible drive shaft 2 is a signal line 5 for a position sensor system which is fashioned as an electromagnetic sensor system. An IVMRI sensor 7 is integrated in the front part of the catheter. In the region of the catheter tip 8 there is located an opening with a cutter 9, which is fashioned as a rotating blade. Located on the catheter tip 8 is a transparent window for the IVMRI sensor 7. Magnetic sensors of the sensor system are also arranged there. These sensors interact with a position sensor 10 which is arranged outside the body of the patient. The position sensor 10 is fashioned as an electromagnetic sensor.

Figure 2:
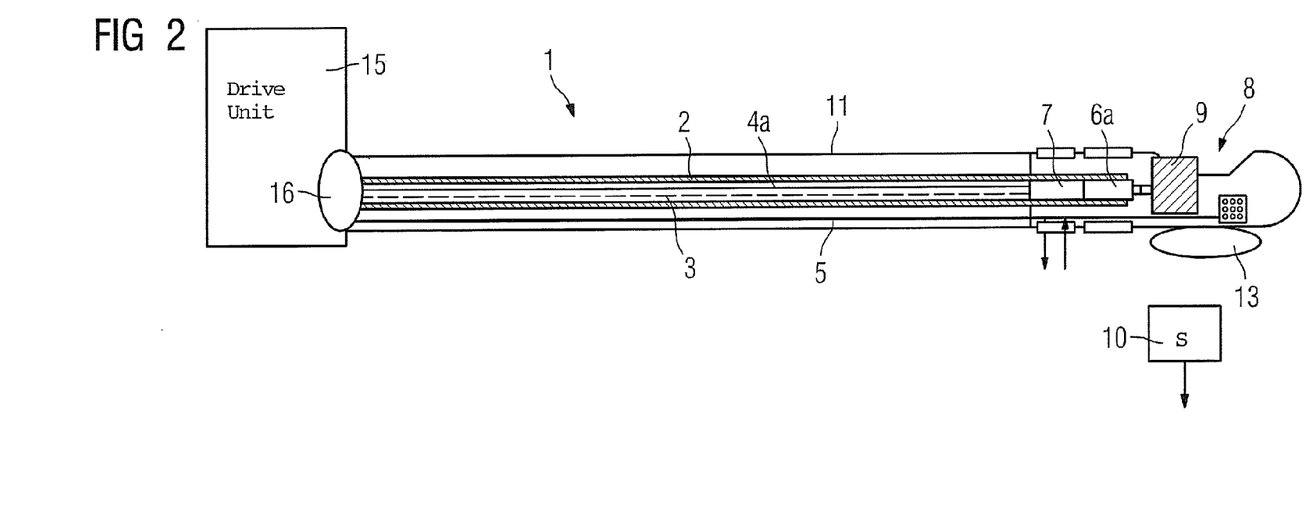

FIG. 2 shows a further catheter device according to the invention, in which those component parts that match those shown in FIG. 1 are labeled with the same reference characters. The catheter device 1 shown in FIG. 2 also has, in contrast to that in FIG. 1, an IVUS sensor 6a with an associated IVUS signal line 4a. With this, it is possible to record, in addition to the IVMRI data, IVUS data in order in this manner to render the deeper tissue layers clearly visible. In this way, the focal points or strengths of the two imaging methods, IVMRI and IVUS, can advantageously be combined in order to obtain an optimum representation of the plaque or vascular wall on which the plaque is removed, as well as of the remaining structures of the area in which the atherectomy is being carried out.

The drive shaft 2 is surrounded by a catheter sheath 11. There is located opposite the opening an expandable balloon 13 to aid positioning.

A signal interface and a drive unit 15 are connected via a rotational coupling 16 to the catheter device 1.

In the catheter device 1 shown in FIGS. 1 and 2, the cutter 9 for performing atherectomy is connected with the IVMRI sensor 7, the IVUS sensor 6a and position sensors to form an integrated device.

Figure 3:
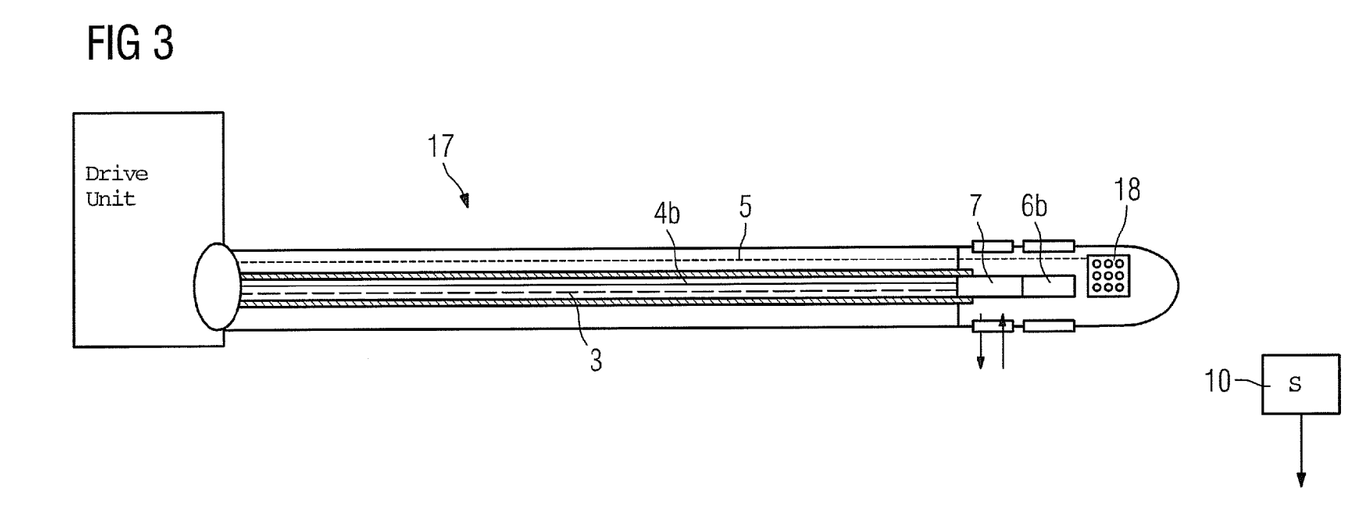
FIGS. 3 and 4 show a further exemplary embodiment of a catheter device according to the invention comprising an IVMRI, an OCT and an IVUS sensor as well as a premounted stent.
Figure 4:
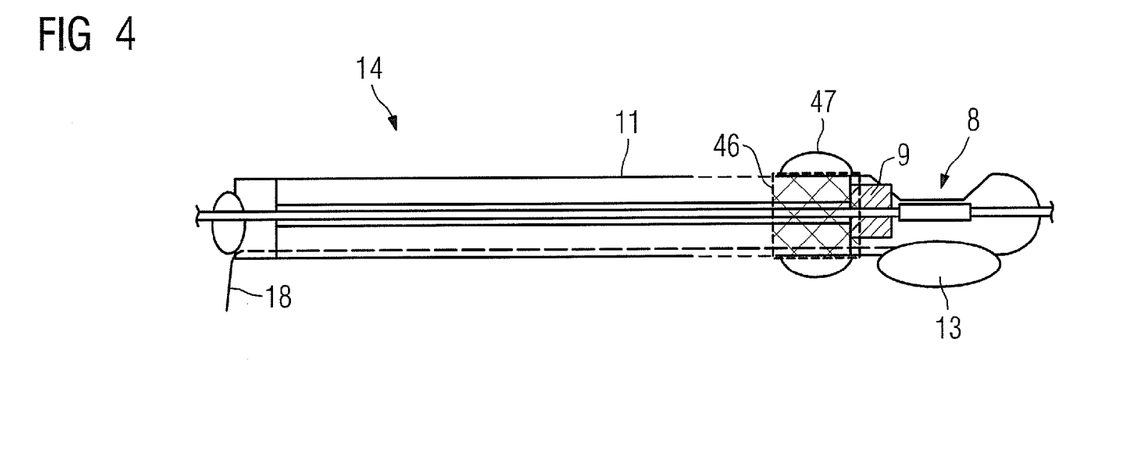

FIGS. 3 and 4 show a further exemplary embodiment of a catheter device.

The same reference characters are used for those components of the catheter device which match those shown in FIGS. 1 and 2.

FIG. 3 shows an imaging catheter 17 comprising IVUS and OCT sensors 6b, an IVMRI sensor 7 with a transparent area for IVMRI, position sensors, signal lines 4b for IVUS and OCT and signal lines 3 for IVMRI. A signal interface and a drive unit 15 are also provided. The IVUS sensor and the OCT sensor are for reasons of clarity shown here as one component with the reference character 6b and a signal line 4b.

FIG. 4 shows an atherectomy catheter 14 which has a lumen into which the imaging catheter 17 can be inserted. Like the catheter shown in FIG. 1, the atherectomy catheter 14 has a cutter 9 in the region of the catheter tip 8 and an expandable balloon 13. In the region of the catheter tip 8, the lumen is transparent for IVMRI as well as for OCT and IVUS. Located inside the catheter 14 is a tube 18 for a pressure medium of the balloon 13.

A premounted stent 46 is also provided which is shown here in the non-expanded position. The stent 46 is furnished with a nano-coating so as not to impede the guiding of the atherectomy catheter 14 through said stent. A balloon 47 can be inflated with compressed air and then causes the stent 46 to deploy. The integration of the stent 46 in the atherectomy catheter 14 advantageously avoids the insertion of a separate catheter for the stent, as a result of which the restenosis risk can be reduced.

The catheter devices 1, 17 shown in FIGS. 1 to 4 each have an IVMRI sensor. In addition, an IVUS sensor is provided in FIG. 2 and in FIGS. 3 and 4 an IVUS and an OCT sensor are provided. The IVMRI sensor supplies particularly good images of the soft-tissue area, i.e. of the affected tissue, the IVUS and OCT sensors supply a good representation of more distant or deeper layers and of the near range.

The catheter devices 1, 17 are connected to an image-processing unit which generates a common image from the images supplied by the sensors. To do this, IVMRI data is used for the affected tissue, a segment of the image optionally supplied by the OCT sensor for the near range, and for the remote range, such as there is, the complementary part of the IVUS image is used, the image data is registered reciprocally by means of the data from the position sensors and fused to form a common image. In this way, sectional images are obtained of the examined vessel, which images can be assigned exactly to a defined position in the body. By means of computerized methods, the data from the position sensor is used to approximate the center line and the envelope curve of the examined vessel. The individual sectional images are then combined to form a volume dataset so that an exact and therefore particularly realistic image is produced.

In approximating the center line of the vessel and the envelope curve of the vessel, the geometric information of the center line is used and combined with the sensor positions recorded during the image recording, as a result of which the artefacts in the 3D image representation are significantly reduced. The 3D coordinates of the center line and the sensor positions recorded during the image recording are subtracted from one another. The result of the subtraction is then used for each of the recorded 2D images in order to obtain an exact 3D reconstruction. This envelope curve of the vessel can be used in further image-processing steps. With the aid of the envelope curve, the 3D-reconstructed IVMRI or IVMRI-OCT-IVUS images are registered and then fused with other anatomical image data, for example, from a 3D-angiographic device of the same vascular section.

The position sensors 10 used in the exemplary embodiments shown in FIGS. 1 to 4 are electromagnetic position sensors, in order to create 3D IVMRI or 3D IVMRI-OCT-IVUS recordings from the 2D IVMRI or 2D IVMRI-OCT-IVUS recordings. The procedure for combining IVMRI with IVUS or OCT alone is analogous. The orientation and position of the catheter in a three-dimensional system of coordinates are recorded by transmitter coils in the object and receiver coils in the room or else conversely with receiver coils in the object and transmitter coils in the room.

The electromagnetic transmitters or alternatively the electromagnetic receivers can be sited in the catheter. Conversely, the corresponding electromagnetic receivers or transmitters can be placed outside the body. Normally, at least one transmitter emitting in the X, Y, Z directions is assigned to a receiver or conversely a receiver receiving from directions X, Y and Z is assigned to a transmitter, so as to enable localization in space. The coils of the electromagnetic position sensors are not arranged exclusively at right angles to one another, but at a random angle of, for example 60° so as to achieve improved miniaturization, which makes it possible for the position sensors to be installed in a catheter.

The image information of the catheter, which information is recorded with the sensors, is fused with or superimposed on other medical images, such as 2D or 3D recordings. The IVMRI or IVMRI-OCT-IVUS images or other combination images of the catheter are displayed together with the X-ray recordings. By this means, the information about the images of the catheter device and the X-ray images are visible to the user together and enable a faster and better diagnosis. In addition, 2D-2D, 2D-3D, 3D-3D and 3D-4D and 4D-4D overlays are possible, in each case the angiographic X-ray images being combined with the images of the catheter device by means of segmentation, registration and image fusion. For the overlaying, images of the following modalities and methods can be used: sonography including IVUS, radiography, screening (fluoroscopy), angiography, OCT, discrete tomography, positron emissions tomography, nuclear medicinal diagnostics, computer tomography, magnetic resonance tomography including intracardial MR, optical recordings including endoscopy, fluorescence and optical markers.

The catheter device is part of a medical treatment device which has a functional unit for eliminating motion artefacts that occur as a result of respiration and the movement of the heart and the blood vessels. In order to eliminate the respiratory artefacts a breastband can also be used which determines the breathing amplitude and frequency via corresponding sensors, so that the image-processing unit can carry out appropriate correction calculations in order to isolate the motion artefacts from the image information.

In order to increase localization precision, the transmitter coils are run with differing frequencies and evaluated cyclically, at defined time intervals. To avoid sensor artefacts which can be generated by superimposing signals from individual sensors, it is proposed that the sensors be read out in temporally offset cycles. For example, the X-ray detectors and the ECG are not read out when the transmitters of the electromagnetic position system are active. The IVMRI sensors and position sensors as well as optionally OCT or IVUS sensors are not read out when the X-ray radiation is active. Thus, read-outs are always only of those signals which are not subject to interference and do not affect any other active sensors.

The functional units and signal lines are fitted with devices and measures which shield the physiological signals and image signals and the signal processing and signal editing against the magnetic filters of the transmitting antennae. To do this, the sheath of the catheter is coated with a thin-film layer composed of conductive nanoparticles. Nanoparticles can also be used in order to effect magnetic shielding.

The catheter sheath is furnished with a coating which reduces frictional resistance when it is being guided through the vessels. This coating can also be based upon nanotechnology or alternatively be produced from a silicon material.

In order to improve the imaging by an IVUS sensor through the use of ultrasound contrast medium, a contrast medium is introduced directly into the vessel to be examined or the body cavity via a channel in the catheter. A contrast medium for imaging by means of IVMRI is introduced in a likewise manner.

A temperature sensor or a pressure sensor is arranged in the tip of the catheter in order to monitor the temperature and the pressure in the vessel or organ to be examined and treated. Any temperature increase that occurs as a result of friction can be recorded by the temperature sensor which is arranged in the tip of the catheter.

Figure 5:
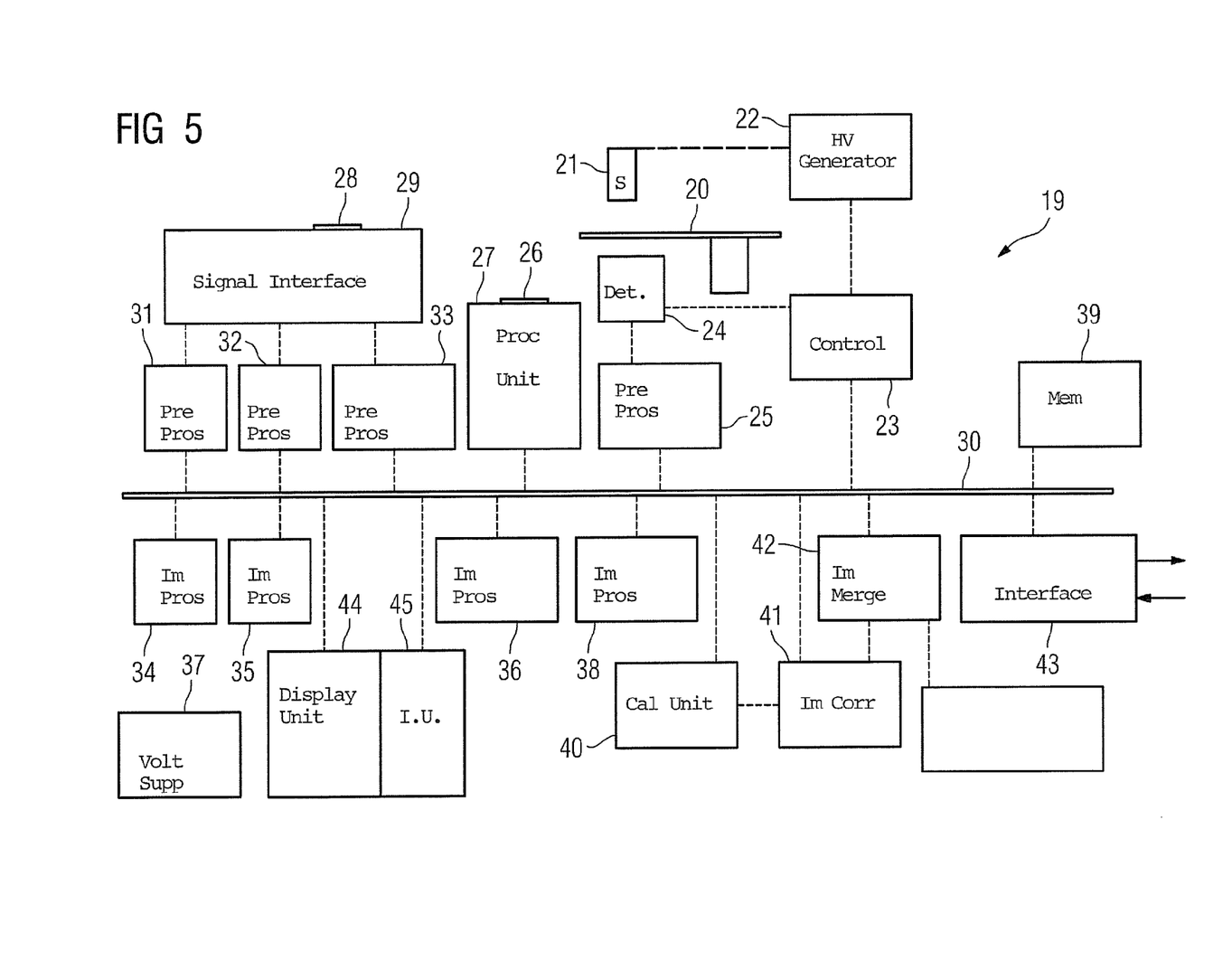
FIG. 5 shows a treatment device according to the invention comprising a catheter device.

FIG. 5 is a schematic representation of a treatment device according to the invention.

The treatment device 19 comprises a catheter device for performing atherectomy. For the treatment, a patient (not shown in FIG. 5) is placed on a patient bed 20, radiation is emitted via a radiation source 21 in the direction of the patient bed 20. The radiation is generated via a high-voltage generator 22 which is controlled via a system control unit 23. An X-ray detector 24 is arranged opposite the radiation source 21, said X-ray detector being in turn connected to a pre-processing unit 25 for X-ray images. There is additionally provided a connection 26 for physiological sensors which is coupled to a physiological signal processing unit 27 in order to monitor ECG signals or pulse signals or the respiration and blood pressure of a patient.

Via a connection 28 for the atherectomy catheter the actual treatment occurs via a signal interface 29 with image monitoring by IVMRI, IVUS and the electromagnetic position sensor system. In addition, a connection exists to a data bus 30. As well as this, pre-processing units 31, 32 and 33 for IVMRI, IVUS and the position sensors are provided. Associated image-processing units 34, 35 and 36 for IVMRI, IVUS and the position sensors are also connected to the data bus 30. The voltage is supplied via a voltage supply unit 37. Furthermore, an image-processing unit 38 for the X-ray images is connected to the data bus 30 which also has a connection to an image data memory 39 for filing and storing the recorded images. A calibration unit 40 and an image correction unit 41 make it possible to take account of imaging interference fields or artefacts. Image merging and reconstruction are carried out in an image merging and/or reconstruction unit 42. Besides this, an interface 43 exists to a patient data and image data system.

The image data obtained from IVMRI, IVUS and the position sensor system and the X-ray images and possible merged images of the various image recording techniques are represented two-dimensionally, three-dimensionally or four-dimensionally on a display unit 44. The display unit 44 is connected to an input unit 45 for inputs by a user with an input unit 45.

Figure 6:
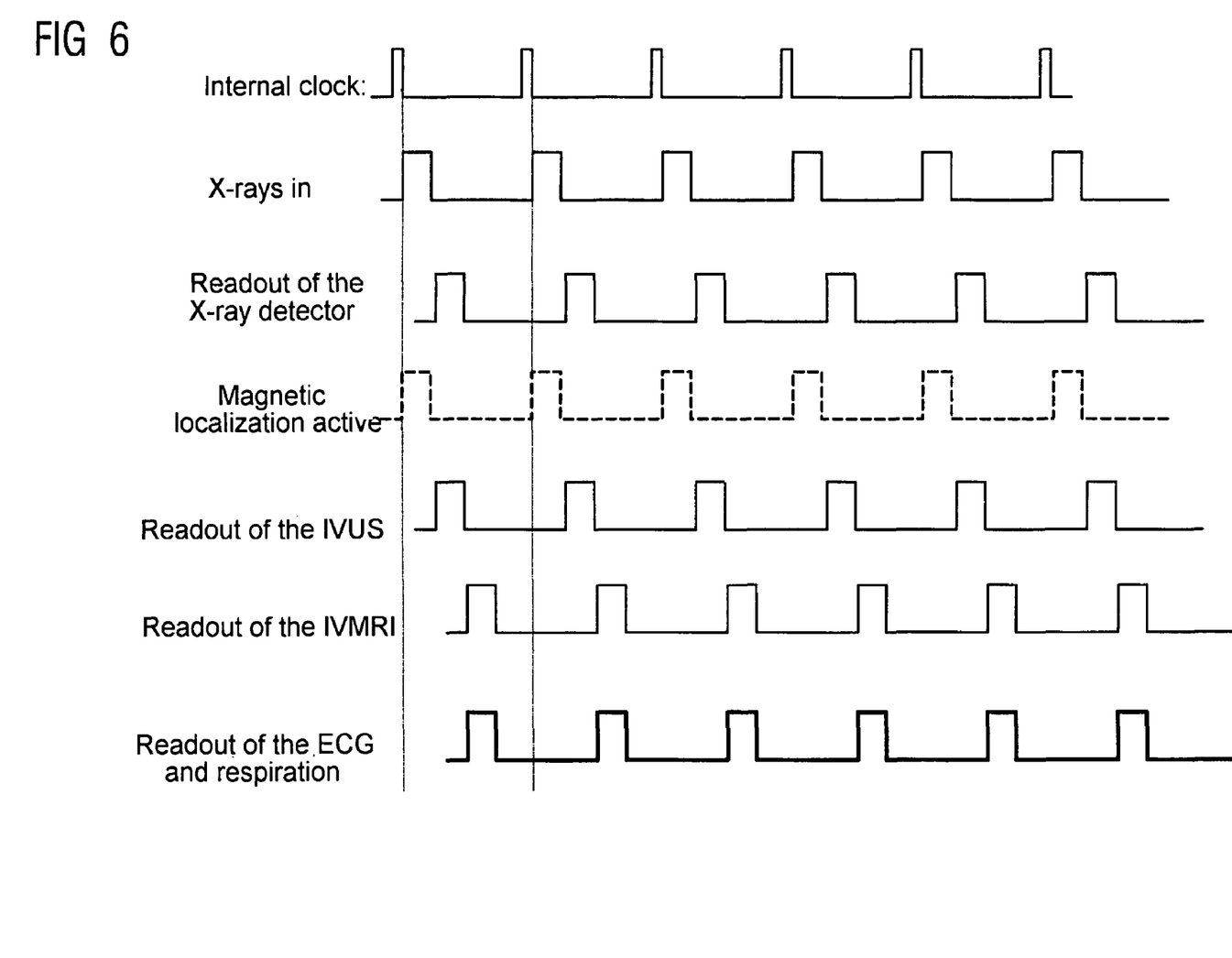
FIG. 6 shows a schematic diagram of the sensor readouts with the treatment device shown in FIG. 5.

FIG. 6 is a schematic representation of the sensor readout of the treatment device when the method according to the invention is being performed.

A typical procedural sequence in cases of a combination of IVMRI and IVUS is as follows: insertion of the catheter under X-ray monitoring, possibly with contrast medium, generation of the angiographic overview recording, generation of recordings of the position sensors, superimposition of the recordings of the position sensors on the angiographic overview by means of segmentation, registration and image fusion, navigation of the catheter, based upon the recordings obtained, to the target position, these steps being carried out partially in parallel and automatically without any user interaction. When the desired target position is reached, the contrast medium for the IVMRI is injected and the stenosis viewed in high resolution two-dimensionally or three-dimensionally by means of the IVMRI-IVUS image recordings. The IVMRI-IVUS recordings are then generated. Subsequently, the IVMRI-IVUS recordings are superimposed on the angiographic overview through segmentation, registration and image fusion. A 3D-reconstruction of the IVMRI-IVUS recordings is then performed, based upon the data from the position sensors. The atherectomy catheter is placed and temporarily fixed in position, for example, by dilating the balloon attached to the catheter tip. Check by means of IVMRI-IVUS in 2D and 3D whether the position and orientation of the atherectomy catheter is correct. Implementation of the atherectomy, i.e. abrasion of the plaque from the vessel wall with the rotating blades. If a certain quantity of plaque is removed, the point in the vessel wall is monitored with the IVMRI sensor. The process is repeated until the plaque has been removed at all points. If necessary, deploying and fastening of a stent. Final monitoring of the atherectomy and extraction of the catheter.

The device according to the invention reduces the method steps required. The IVMRI sensor supplies good recordings of the affected tissue, the IVUS sensor adequately good images of deeper-lying tissue layers. 3D recordings can be generated from the IVMRI and IVUS recordings by means of the electromagnetic position sensors. In addition, after the performance of an angiographic overview through corresponding use of the signals from the position sensors, the path of the catheter can be mapped solely from the IVUS, IVMRI and electromagnetic signals, i.e. the amount of X-radiation can be cut. The system provides important additional medical information about the arteriosclerotic plaque. In addition, the correct orientation of the tip of the catheter can be better checked by this means. The device enables a very good check to be carried out of the correct orientation in particular of the tip of the atherectomy catheter.

The sensors of the medical treatment device, which in the exemplary embodiment shown is an X-ray installation, are read out in part in temporally offset cycles. Firstly a system cycle is specified in which individual system pulses are generated, the switching-on of the X-radiation and activation of the magnetic localization being connected to this pulse generation. After the X-radiation has been switched off, the X-ray detector read-out is obtained and at the same time the IVUS data is read out. Following this, the IVMRI data is read out, this occurring at the same time as the reading out of the ECG and of the data on respiration. In this way, the individual sensors are read out or the components of the catheter device controlled such that mutual interference can be excluded. The temporally offset and clocked reading out shown here is thus to be seen as an example for obtaining a read-out while avoiding disruptive influences.

The invention claimed is:

1. A catheter device for performing an atherectomy on a patient, comprising:
an atherectomy catheter;
an intravascular magnetic resonance tomography (IVMRI) sensor integrated with the atherectomy catheter that generates data of a target area of the patient;
at least a second sensor which includes an OCT sensor or an IVUS sensor or a combination of the OCT sensor and the IVUS sensor,
a position sensor integrated with the atherectomy catheter that generates data of a position of the atherectomy catheter; and
an image-processing unit that:
reads out the data of the position sensor and the data of the IVMRI sensor temporally offset to avoid mutual interference, and reads out data of at least the IVMRI sensor and the second sensor temporally offset to avoid mutual interference of data acquired from two different sensors, which image data are combined with position sensor data by the image-processing unit to form a combined image recording of the target area, the combination enabling recordation of image data which renders tissue layers visible with use of the IVMRI sensor and renders deeper tissue layers visible with the second sensor thereby providing an optimum representation of plaque or of a vascular wall on which plaque is removed.

2. The catheter device as claimed in claim 1, wherein the combined image recording is a 2D or 3D image recording.

3. The catheter device as claimed in claim 1, wherein the catheter device comprises a lumen for introducing an MRI contrast medium.

4. The catheter device as claimed in claim 1, wherein the catheter device is automatically pushed forward or pulled back at a specifiable speed by a drive unit.

5. The catheter device as claimed in claim 1, wherein the catheter device is controlled:
mechanically by a pulling wire, or
magnetically by an external magnetic field, wherein the catheter device comprises a permanent magnet or an electromagnet.

6. The catheter device as claimed in claim 5, wherein the position sensor is arranged at a tip of the catheter device and is an electromagnetic sensor comprising:
a transmitter coil in the catheter device and an external receiver coil, or
an external transmitter coil and a receiver coil in the catheter device.

7. The catheter device as claimed in claim 6, wherein the receiver coil comprises an iron core and is used as a receiving antenna or an electromagnet for a magnetic navigation.

8. The catheter device as claimed in claim 6,
wherein the catheter device comprises a plurality of transmitter coils or a plurality of receiver coils,
wherein the transmitter coils or the receiver coils in the catheter device are arranged orthogonally or at an angle, and
wherein the angle is 60°.

9. The catheter device as claimed in claim 1, wherein the IVMRI sensor, or the OCT sensor, or the IVUS sensor, or a combination thereof is:
oriented laterally relative to a longitudinal axis of the catheter device, and
rotated separately or together about the longitudinal axis of the catheter device.

10. The catheter device as claimed in claim 1,
wherein the image processing unit:
approximates a center line or an envelope curve of the target area of the patient, and
registers and fuses a 3D image recording of the catheter device with an anatomic image data of the patient according to the center line or the envelope curve,
wherein the anatomic image data is selected from the group consisting of: a 3D angiography data, a computer-assisted tomography data, a nuclear magnetic resonance tomography data, and
wherein the 3D image recording of the catheter device and the anatomic image data is translated into a common coordinate system.

11. The catheter device as claimed in claim 1, wherein the catheter device comprises a coating for:
shielding against an electromagnetic field, wherein the coating is a thin film layer comprising a conductive nanoparticle, and
reducing a friction, wherein the coating comprises a silicon material or a nanomaterial.

12. The catheter device as claimed in claim 1, wherein the catheter device and the sensors are electrically isolated from a main voltage.

13. The catheter device as claimed in claim 1, further comprising:
an x-ray marker,
an inflatable balloon arranged at a tip of the catheter device that supports positioning the catheter device,
a temperature sensor or a pressure sensor arranged at the tip of the catheter device.

14. The catheter device as claimed in claim 1 wherein the catheter device includes a tip, the catheter device further comprising a stent that is premounted in a region of the tip of the catheter device, wherein the stent is:
partially self-deployed, or
deployed by an expandable balloon arranged in the region of the tip of the catheter device.

15. The catheter device as claimed in claim 14,
wherein the stent comprises a metal or bioabsorbable material,
wherein the metal material is selected from the group consisting of: a stainless steel, a nitinol, and a memory-metal alloy, and
wherein the bioabsorbable material is selected from the group consisting of: a biological material, a magnesium material, a bio-engineering material, and a plastic.

16. The catheter device as claimed in claim 14,
wherein the stent comprises a coating,
wherein the coating is a nano coating or a active component coating, and
wherein the active component coating is selected from the group consisting of: sirolimus, paclitaxel, everolimus, rapamycin, FK 506, and a growth inhibitor.

17. A method for generating an examination image of a patient during an atherectomy treatment, comprising:
integrating a position sensor and an IVMRI sensor and at least a second sensor which includes an OCT sensor or an IVUS sensor or a combination of the OCT sensor and the IVUS sensor, into an atherectomy catheter;
connecting the position sensor and the IVMRI sensor and the second sensor to an image-processing unit;
temporally offset reading out data from the position sensor and the IVMRI sensor and the second sensor by the image-processing unit to avoid mutual interference; and
generating a combined image recording of the patient based on the data from the position sensor and the IVMRI sensor and the second sensor by the image-processing unit.

18. The method according to claim 17, wherein a motion artifact arisen by a respiration or a motion of a moving organ of the patient is determined by recording a frequency or an amplitude of the movement and is computationally corrected.

* * * * *